(12) United States Patent
Ferrer et al.

(10) Patent No.: US 6,364,854 B1
(45) Date of Patent: Apr. 2, 2002

(54) APPLICATOR FOR SEMI-SOLID MEDICATIONS

(75) Inventors: Francisco Ferrer; José Ignacio Izquierdo; Javier Forn; Javier Segado, all of Barcelona (ES)

(73) Assignee: J. Uriach & CIA. S. A. (ES)

( * ) Notice: Subject to any disclaimer, the term of this patent is extended or adjusted under 35 U.S.C. 154(b) by 0 days.

(21) Appl. No.: 09/355,689

(22) PCT Filed: Feb. 6, 1998

(86) PCT No.: PCT/EP98/00674

§ 371 Date: Sep. 7, 1999

§ 102(e) Date: Sep. 7, 1999

(87) PCT Pub. No.: WO98/34671

PCT Pub. Date: Aug. 13, 1998

(30) Foreign Application Priority Data

Feb. 7, 1997 (ES) .............................................. 97 00252

(51) Int. Cl.[7] .......................... A61M 31/00; A61F 13/20
(52) U.S. Cl. ............................. 604/60; 604/11; 604/288
(58) Field of Search ........................ 604/11–18, 57–60, 604/285–288, 385.17, 385.18, 904

(56) References Cited

U.S. PATENT DOCUMENTS 2,630,804 A * 3/1953 Mende
4,636,202 A * 1/1987 Lowin et al. ............... 604/236
5,531,703 A * 7/1996 Skwarek et al. ............ 604/187

FOREIGN PATENT DOCUMENTS

WO    WO 93/21986    11/1993

* cited by examiner

*Primary Examiner*—Dennis Ruhl
(74) *Attorney, Agent, or Firm*—Schnader Harrison Segal & Lewis LLP

(57) ABSTRACT

An applicator for semi-solid medications comprises a tubular body (20) having a rounded dispensing end (21) provided with at least one opening (26) and a grasping end (22), the inner surface of a proximal portion of said tubular body defining a reservoir for the medication, a plunger (30), initially housed inside the tubular body, which plunger is provided with a rod (31) and grasping means (33), a piston (40), positioned in sealing contact with the inner surface of said tubular body providing a closure for the medication reservoir, wherein said piston has a longitudinal hole (45) through which rod (31) of the plunger is disposed, and wherein said piston initially abuts on a stop means (25) when the applicator is received by the user, a coupling means (35, 46) between rod (31) and piston (40), a closure means for sealingly closing off said opening (26) on said dispensing end, wherein the plunger (30) is extractable from the tubular body until the rod (31) becomes engaged with the piston (40) by the coupling means, whereupon the plunger together with the piston is displaceable along the tubular body towards the dispensing end (21) for expelling the medication through opening (26), and wherein the stops means (25) is provided in the form of a projection on the inner surface of the tubular body.

Figure 1:
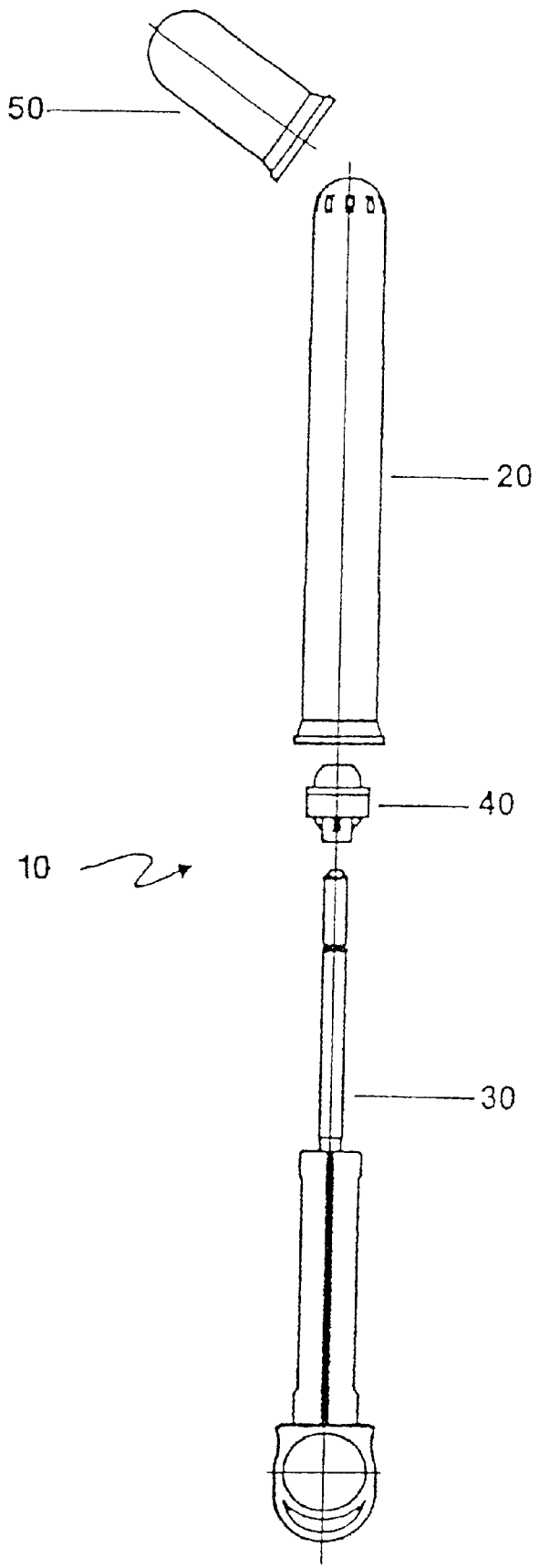

17 Claims, 5 Drawing Sheets a  b  c

APPLICATOR FOR SEMI-SOLID MEDICATIONS

FIELD OF THE INVENTION

This invention relates to a new applicator, and more specifically to a new prefilled applicator for administration of semi-solid medications such as creams and the like to the vagina and other body cavities.

DESCRIPTION OF THE PRIOR ART

The use of vaginal applicators for application of medication is well known in the art. There are currently a number of applicators on the market for application of semi-solid medications to the vagina. In general, compliance of vaginal treatments with medications of this type is largely dependent on the applicator used. It is therefore necessary to employ applicators that are as comfortable and easy to operate for the user as possible and that do not produce irritation or pain. They must also fulfill a number of additional requirements, such as simplicity and economy of manufacture. It is also very important that they can be used both as a container for the medication and as a device for dispensing the medication, thus avoiding any handling by the user. This handling, apart from being cumbersome and messy, makes it impossible to guarantee the hygienic conditions necessary for this type of device and that the correct dosage of the medication is applied. In order to be used as a container, the device must seal off the compartment where the medication is stored. In this case, it is also important for the applicator to be easy to fill with the medication at the factory.

Most applicators on the market do not fulfill many of these requirements. They usually comprise a straight, hollow cylindrical body with a small diameter and a plunger stem movable within the cylinder, and they are usually intented for repeated use. One of the ends of said cylinder is open and generally contains an inner thread, allowing it to be threaded to a tube containing the vaginal medication. In order to use the applicator, the medication tube must be screwed into the open end of the applicator. The opposite end of the tube is then squeezed, forcing the medication into the applicator. Then, the tube is unscrewed and the applicator is ready for use. This type of applicator cannot be used as a container, i.e, they cannot be prefilled with the medication, because they do not provide an air-tight seal, which means that the user must fill the applicator before each use, with the resulting possibility of error in dosage, hygiene loss and the inconvenience of the loading process for the user.

Some applicators suitable for being prefilled with medication have been described in the literature.

U.S. Pat. No. 2,630,804 discloses a prefilled vaginal applicator wherein for compactness purposes the body of the applicator is provided as a telescoping assembly comprising inner and outer tubes. A piston is disposed closing one end of said inner tube and the other end is closed by means of a plug. A telescoping piston rod is disposed inside the inner tube, through a hole in the piston. In use, telescoping rod assembly must be first extended, then telescoping barrel assembly must be extended to its full length by sliding outer barrel along inner barrel, and finally extended piston rod must be pulled and brought into locking engagement with the piston. While providing a compact device, this applicator is difficult to use, since three operations are needed to assemble the applicator before use, and there is also a risk of disassembling the telescoping barrels during use if the user pulls too strong during the second operation. Moreover, this applicator may cause discomfort during use since it is not rounded at its dispensing end.

U.S. Pat. No. 4,636,202 describes a vaginal applicator provided with an automatically-opening closure for the dispensing end of the applicator body.

WO 93/21986 describes a vaginal applicator comprising a barrel having a large diameter cylindrical section, a small diameter section and a sloped transition section together with a twist off cap and a rubber plunger provided with a piston rod. The twist off cap is used both to close the dispensing end and as a rod to push the piston rod and expel the medication. In use, the cap must be removed by twisting it off, then must be inverted and reinserted within the large diameter section, and pushed to expel the medication. This applicator is difficult to use since it involves disassembly and reassembly of the cap.

For these reasons, a new, improved vaginal applicator is necessary that can solve these and other problems that will become clear throughout the description.

DESCRIPTION OF THE INVENTION

It is the object of the present invention to provide a vaginal applicator that can be used both as a container and a device for dispensing the medication, which contains a minimum number of parts, which is inexpensive to manufacture and easy to assemble and fill with the medication in the factory as well as easy and convenient to operate for the user.

This object is achieved by the features of claim 1.

Figure 2:
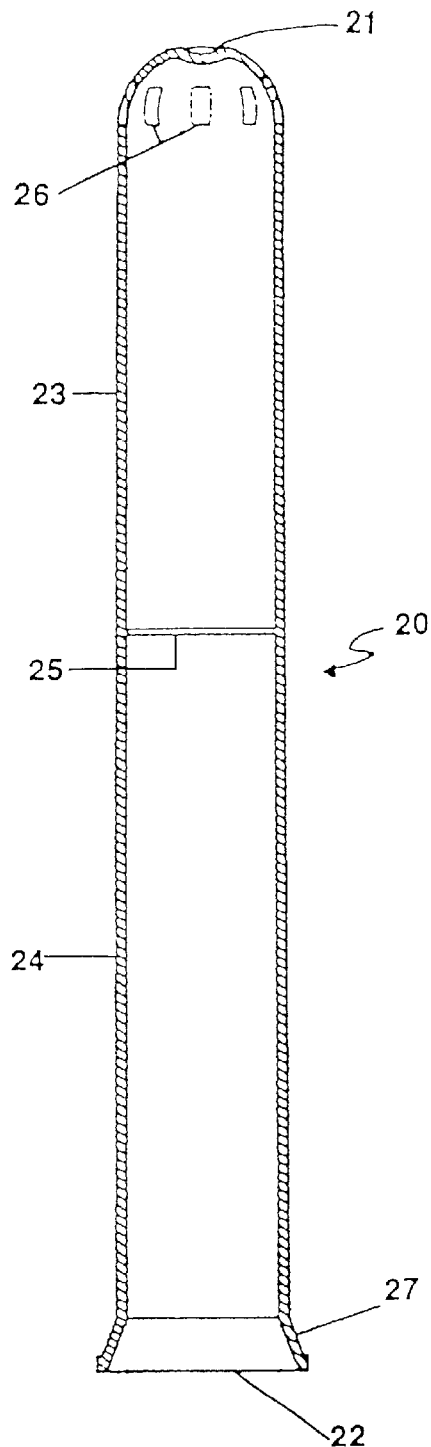
Figure 3:
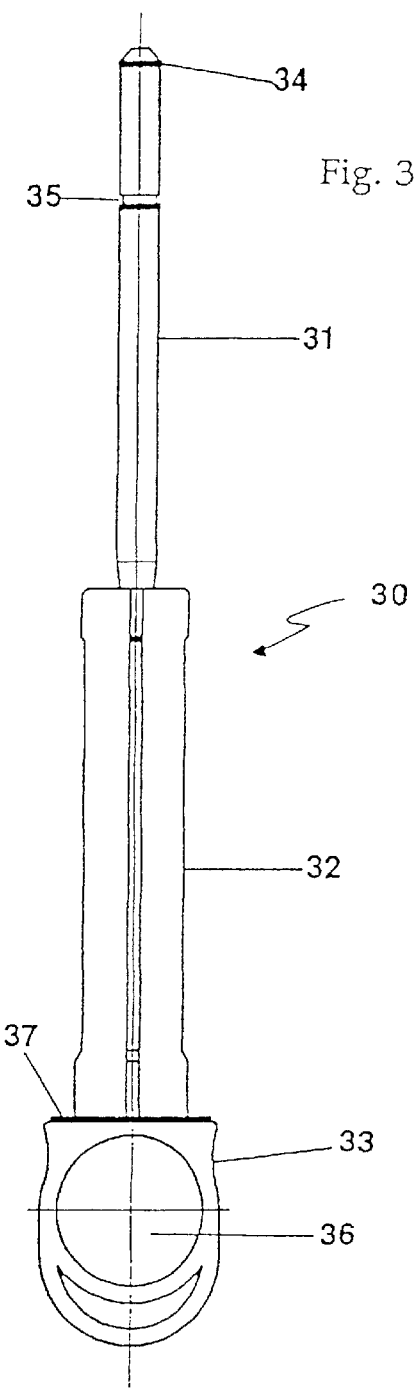
Figure 4:
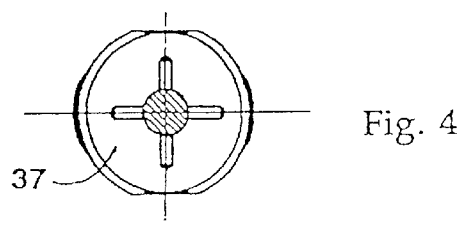
Figure 5:
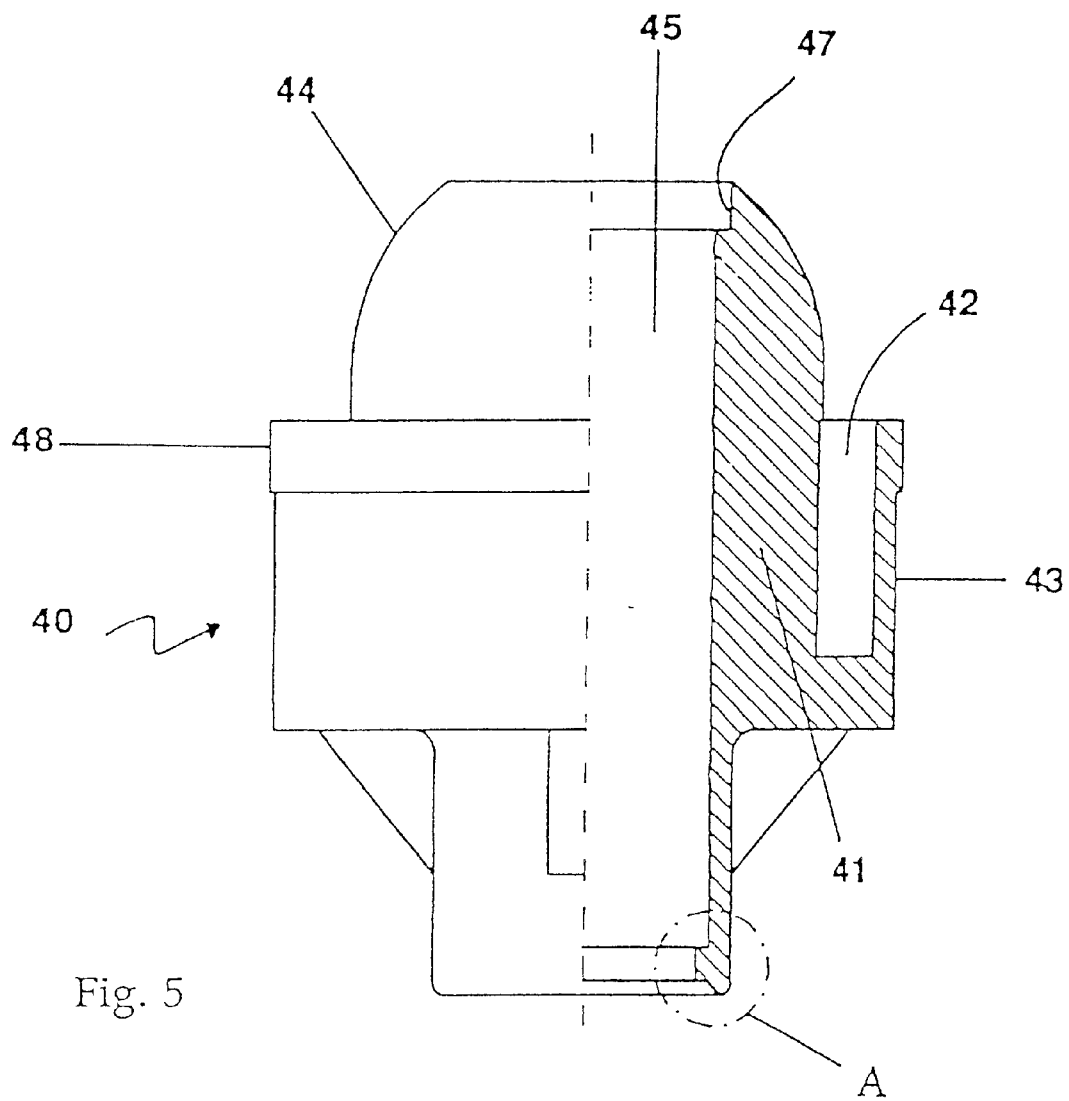
Figure 6:
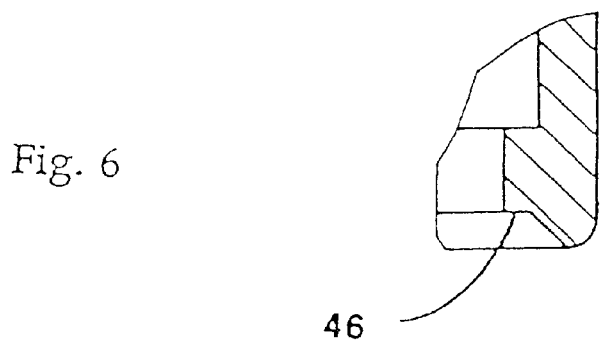
Figure 7:
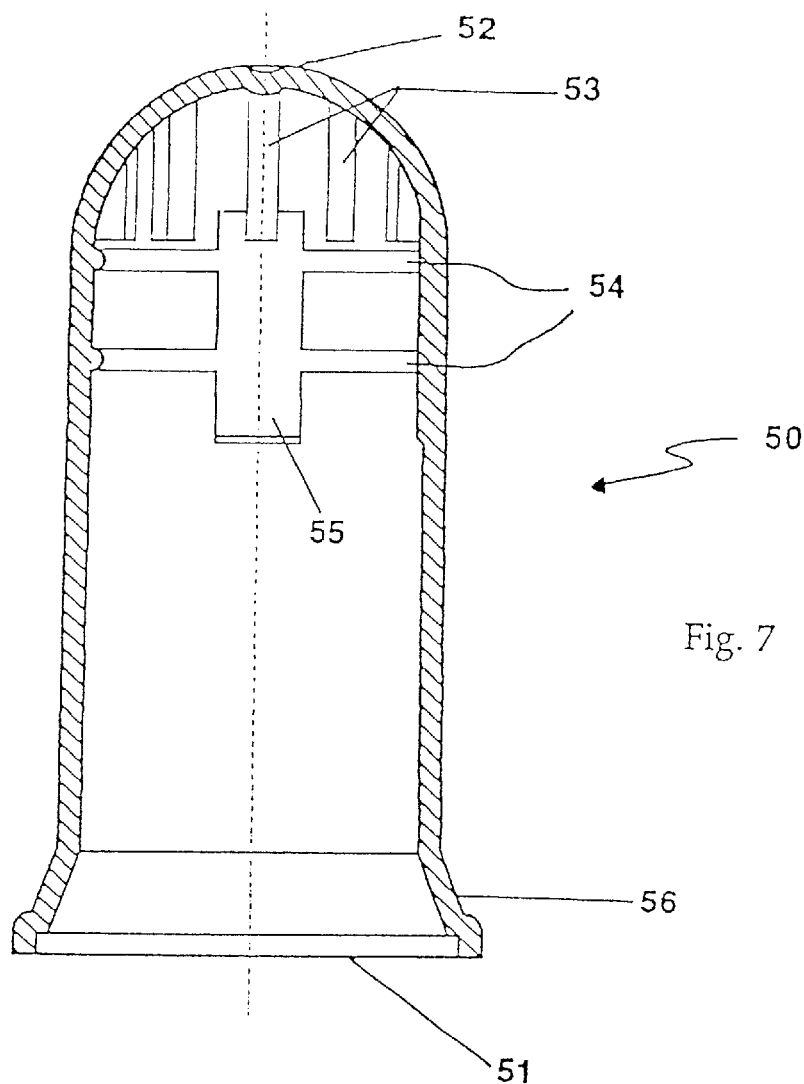
Figure 8:
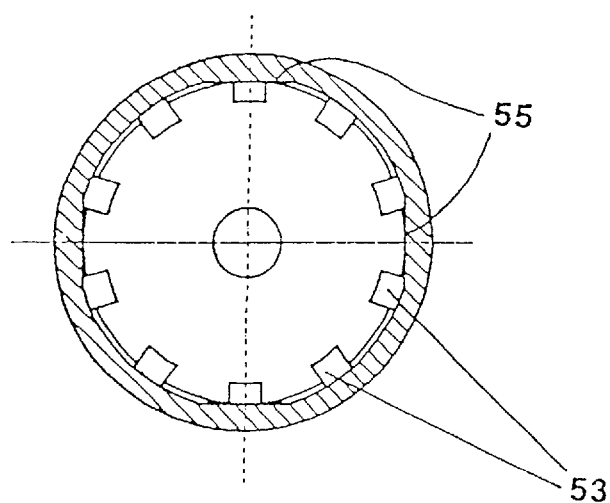
Figure 9:
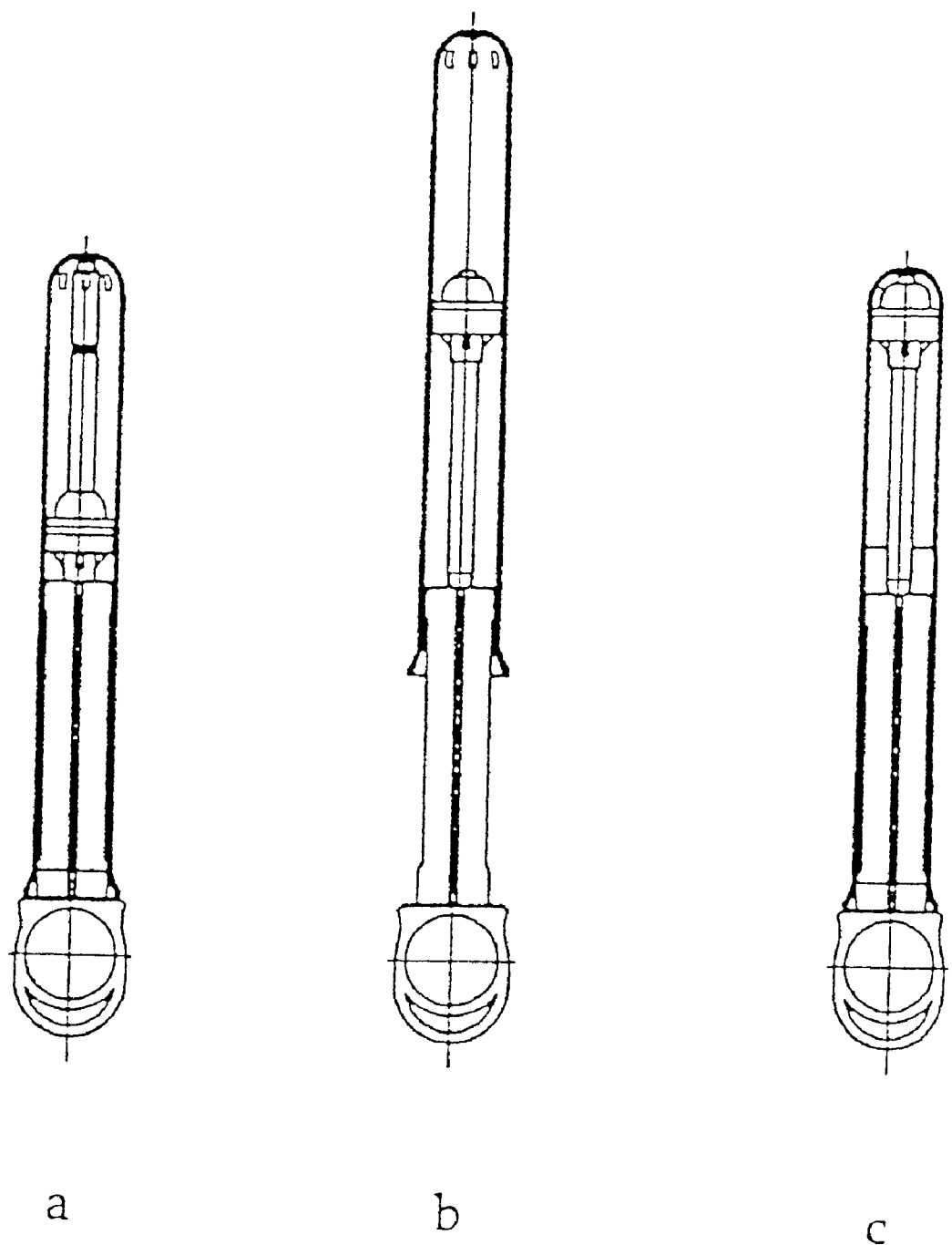

An example according to the invention is explained in more detail in connection with the drawings, wherein:

FIG. 1 is a exploded view of the various parts of an applicator according to the present invention, FIG. 2 is a longitudinal section of the hollow tubular body of the applicator, FIG. 3 is a side view of the plunger, FIG. 4 is a front elevational view of the plunger of FIG. 3, FIG. 5 is a partial cross-section of the piston, FIG. 6 is a detailed view of element A in FIG. 5, FIG. 7 is a longitudinal section of the cap, FIG. 8 is a cross-section of the cap of FIG. 7, and FIG. 9 shows the applicator of the invention in different positions during use; (a) applicator in the initial compact position, as received by the user; (b) applicator showing the plunger and piston in an assembled position, ready to discharge the medication; (c) applicator after use, showing the assembled impeller means fully depressed. To facilitate comprehension of the drawings, representation of the cap has been omitted.

As illustrated in FIG. 1, a vaginal applicator 10, in accordance with this invention, essentially consists of four parts: a main tubular body 20, a plunger 30 and a piston 40, which together constitute the impeller means for expelling the contents, and a cap 50.

As mentioned above, this applicator is designed to be used both as a container and as a device for applying the dose of medication to be administered. To guarantee operation, a rigid material must be used for the main body 20 and a flexible material for the piston 40.

The main body 20 has a closed dispensing end 21 and an open grasping end 22, as illustrated in FIG. 2. This body serves as a reservoir for the medication and also contains the impeller mechanism housed inside.

This main body 20 is formed by an essentially cylindrical hollow tube that is differentiated into two portions 23 and 24, formed coaxially and integrally with each other, which are separated by an annular projection 25 formed on the inner wall of the body 20. This projection or rib 25 serves to retain the piston in the initial, non-operating, compact position of the applicator, as described below.

The proximal portion of the main body 23, close to the dispensing end 21, is formed by a cylindrical section with a constant diameter. The internal cavity of this section constitutes the reservoir for the medication. This section ends in a closed free end that is rounded 21, which facilitates insertion of the applicator 10 into the vagina, without discomfort or irritation for the user. This rounded end 21 has a plurality of openings 26, preferably arranged equidistantly, which allow for radial discharge of the medication when the plunger-piston mechanism is activated, thus providing better distribution of the medication in the area being treated. As will be evident to those skilled in the art, it is possible to modify the number of openings and their shape and size, and all these modifications form part of the scope of this invention.

The distal portion 24 of the main body 20 is also cylindrical, and at its open distal end 22, a radially outwardly extending annular flange 27 is formed on the outer surface of the applicator body, which serves as a support to help the user hold the applicator during use. In a preferred embodiment, the diameter of this distal portion 24 widens slightly in the direction of the distal end 22 of the applicator body, so that at the end 22 the diameter is slightly larger than the diameter in the central area near the annular projection 25. This arrangement makes it possible to evacuate the air contained in the applicator during assembly of the applicator, as explained below. Because the diameter of section 24 is larger than that of the piston, the piston can move easily and without friction to the retaining point in the form of annular projection 25 located in the central area of the applicator, thus allowing the air to escape. If the diameter were constant throughout the entire body of the applicator, the piston would seal against the wall of the applicator at all times, thus impeding the evacuation of the air contained inside. The increase in diameter of section 24 may be so small that although sufficient to allow air to escape, it may not be visually detectable.

The impeller mechanism for expelling the medication slides inside the cylindrical tube of the applicator. This mechanism consists of a system of plunger 30 and piston 40.

The plunger 30 has three parts, moulded as a single piece, as shown in FIGS. 3 and 4; one end 31, to which we will refer as the inner end because it is always housed inside the main body 20, a centre part 32 and an outer end 33. The inner end 31 is formed by a cylindrical rod with a diameter that is much smaller than the body 20, suitable for slidably moving through the piston as described below, and which has an apical annular rib or projection 34. At a certain distance, which will depend on the size of the piston, there is an annular groove 35. The rib 34 and groove 35, respectively, serve to interact with the piston to lock it in the operating or extended position of the plunger-piston system, ready to discharge the medication. This cylindrical rod 31 is the prolongation of a cruciform shaped rod 32, which is slightly smaller in width than the interior diameter of the applicator body, but large enough to make contact with the interior of the applicator and retain the plunger 30 in the initial compact or retracted position of the applicator. This cruciform design has been used for this part because it provides the greatest rigidity and stability with the minimum amount of material. However, it should be evident to the skilled person that other designs for this part are possible, all of which are included in the scope of the present invention. This cruciform shaped rod 32 is provided at its end with grasping means 33 to facilitate the operation of the plunger-piston system while the applicator is in use, which in the preferred embodiment shown in the drawings is shown as an essentially circular ring 33 with an orifice 36 for the insertion of a finger. The junction between 32 and 33 is moulded in the shape of a disk 37, which serves to limit the advance of the plunger-piston system inside the body 20 while the medication is being expelled.

The length of sections 31 and 32 is such that when the disk 37 is applied against the end 22 of the body 20 in the operating position of the impeller mechanism, i.e. when plunger and piston are assembled, the piston 40 is located at the dispensing end 21 and virtually all the medication will have been discharged, as shown in FIG. 9c.

The piston 40, shown in FIG. 5, is designed to be assembled with the plunger 30 and constitute the impeller system for expelling the medication. The piston 40 fits snugly within section 23 of the applicator body, thus providing a closure to the compartment where the medication is stored, and when the applicator is received by the user it abuts on annular projection 25. The piston 40 includes an essentially cylindrical central section 41, which constitutes the body of the piston, a channel 42 and, a circumferential sealing edge or flange 43. In the preferred embodiment, shown in FIG. 5, the central section 41 ends in a rounded projection 44, which is similar in shape and size to the rounded end of the applicator, so that the maximum amount of medication possible can be expelled. As will be apparent to those skilled in the art, it would be possible to use a piston in which the central section 41 is flat, but in that case the effectiveness of the discharge would be less because part of the contents would not be dispensed.

The central section 41 of the piston has a longitudinal orifice running through it 45, as shown in FIG. 5, with a diameter that is slightly larger than that of the rod 31 of the plunger, which allows for the assembly and operation of the plunger-piston impeller system. At the bottom end of this orifice there is an annular projection 46 shaped in the wail so that the diameter of the orifice 45 at this point is slightly smaller than that of the rod 31, as shown in FIG. 6. The reduction of the diameter corresponds approximately to the dimensions of the groove 35 on the rod 31 of the plunger. As shown in FIG. 5, at the upper end of the orifice 45, the diameter increases slightly, forming a recess 47, so that the increase in diameter corresponds exactly to the apical annular rib 34 of the plunger. In this way, the pairs of elements 46-35 and 47-34 act by retaining the piston in an engaged position at one end of the plunger, allowing the discharge of the medication and avoiding accidental disassembly of the plunger-piston system while the applicator is being used.

The piston also includes a sealing flange or edge 43 for the purpose of sealing against inner walls of tubular body 20, which completely encircles the central section 41, leaving a channel 42 between them. This flange 43 has an annular lip 48 on its outer surface that fulfills two functions. On the one hand, it interacts with the annular projection 25 of the main body 20, fixing the plunger-piston impeller system in the initial compact position of the applicator and defining the reservoir for the medication. On the other hand, because of its flexibility, provided by the construction material and the channel 42, it can be proportioned so that its size is slightly greater than the inner diameter of the section 23 of the applicator body, thus providing a tighter seal of the compartment where the medication is stored, and making it possible to expel all the medication in contact with the inner walls of the applicator, without impeding at the same time smooth sliding movement of the piston within section 23 while the applicator is being used.

When the piston 40 abutting on the cruciform-shaped section 32 is inserted into the prefilled tubular body 20, the lip 48 of the piston passes over the annular projection 25, so that the lower edge of lip 48 in FIG. 5 abuts on the annular projection 25 for holding the piston 40, when the plunger is retracted, as shown in FIG. 9b, until the rod 31 is coupled with the piston 40 by means of groove 35 and annular projection 46.

The distance between annular projection 25 and outer end 22 of the tubular body corresponds essentially to the distance between disc 37 and lower edge of lip 48, when the piston 40 abuts on the cruciform-shaped section 32 in FIG. 9a. In this position the rod 31 extends to the dispensing end 21 of the tubular body.

The portion 24 of the tubular body is preferably longer than the portion 23, so that in the position of FIG. 9b the cruciform-shaped section 32 is guided within portion 24 over a short distance.

The applicator 10 further includes a cap 50 which covers the dispensing end. The function of this cap is to sealingly close off the dispensing openings 26. As is shown in FIGS. 7 and 8, cap 50 has essentially the same shape as the dispensing end and includes a cylindrical body that is open at one end 51 and closed at the opposite end 52. In a preferred embodiment, shown in the drawings, there are provided projections 63 on the inner surface of the cap 50, whose size, shape and number correspond to those of the openings 26 on the dispensing end of the applicator, so that they fit perfectly into these openings and provide a tight seal which prevents the medication contained in the applicator from leaking out. As shown in the preferred embodiment described in the drawings, to improve the seal, one or more inner annular projections 54 can be optionally arranged in parallel on the inner wall of the cap to fit against the outer wall of the applicator body, thus providing a more effective seal. Finally, to ensure that the cap 50 is properly secured on the dispensing end, longitudinal ribs 55 can be optionally arranged on the inner surface of the cap, distributed equiangularly and the number of which can vary within the scope of this invention. Just as an example, FIGS. 7 and 8 show a cap having four of these ribs 55. The open end 51 of the cap 50 flares out forming a radially outwardly extending annular flange 56 to aid the user in removing the cap.

The assembly of the applicator is performed by assembling two by two the above elements as described below.

First, the piston 40 and plunger 30 are coupled. Specifically, the rod 31 of the plunger is passed through the orifice 45 of the piston until the piston makes contact with the cruciform shaped section 32 of the plunger. Because the piston is made of a relatively flexible material, it easily deforms under the pressure applied to introduce the rod 31, so that the latter can be passed through the piston, even though the apical annular rib 34 of the rod has a larger diameter than the piston orifice 45 itself.

Next, the cap 50 is fixed on the dispensing end 21 of the applicator body 20.

The body-cap unit is placed in the vertical position so that the open end 22 is facing upward and a predetermined amount of the medication to be administered is dispensed through open end 22 so that it is stored in the proximal portion 23 of the applicator body.

The assembled plunger-piston system is then introduced through open end 22 and pressed until lip 48 passes over the annular projection 25. At this moment the disk 37 of the plunger will rest against the end 22 of the applicator. Because section 24 of the main body 20 is slightly conical, as described above, the piston 40 does not seal off the compartment where the medication is stored until it abuts on annular projection 25, so that the air inside the applicator can be evacuated, thus avoiding extra pressure in the medication compartment and making it possible to store the vaginal medication in an air-tight substantially air-evacuated environment.

At this point, the applicator is assembled and ready to be used. As it will be apparent to those skilled in the art, because the impeller mechanism is housed inside the body of the applicator, the applicator of the present invention represents a truly compact device which occupies a minimum amount of packaging space.

The device described in this invention is very easy and convenient to use, mainly because its tip is rounded, meaning that it does not produce irritation or pain during its use, and because it does not require complicated handling by the user before being put to use. The mode of use of the applicator of the present invention, which is prefilled with the desired amount of medication, can be described in two stages, as illustrated in FIG. 9:

1. Assembly of the plunger-piston impeller system:

While holding the applicator 10 in the initial compact position shown in FIG. 9a in one hand, the index finger of the other hand is inserted through the ring 33 of the plunger and this is pulled smoothly and slowly outward, making the rod 31 of the plunger pass through the orifice 45 of the piston until the piston engages with the plunger. At this point, the groove 35 and the annular rib 34 of the plunger will have fit into locking engagement with the annular projection 46 and recess 47 of the piston, respectively, thus fixing the piston at one end of the plunger, as shown in FIG. 9b.

2. Discharge of the medication:

The cap 50 is removed and, holding the applicator at the end 22 between the thumb and remaining fingers and with the index finder through the ring 33, the applicator is inserted into the vagina as deeply as possible with the rounded end 21 first. In general, the user will have an indication that the applicator has been inserted to the appropriate depth when the fingers holding the end 22 make contact with the area surrounding the vaginal orifice. It must be borne in mind, however, that the depth of insertion may vary in some women based on the size of their vagina, so that the insertion of the applicator should always be kept within the comfort limits of the user.

Once the applicator has been inserted, the ring 33 is pushed with the index finger toward the dispensing end 21, causing the piston to exert pressure on the medication, which then flows through openings 26 into the vagina The ring 33 should be pushed as far as possible, i.e., until the disk 37 contacts the end 22 of the applicator body as shown in FIG. 9c. In this way, virtually all the medication will have been dispensed. At this point, the applicator is withdrawn and discarded.

As will be apparent to those skilled in the art, the present invention is not limited to the preferred embodiment shown in the attached drawings, but can be modified and changed in different ways, e.g., the dimensions and materials, within the scope of this invention.

Furthermore, the applicator of the present invention can be used to administer medications to body cavities other than the vagina, such as the anus, in which case it may be necessary to modify the diameter and/or length of the applicator to adapt it to these uses.

What is claimed is:

1. An applicator for a semi-solid medication comprising:
a tubular body having a closed rounded dispensing end provided with at least one opening and an open grasping end, wherein the rounded dispensing end is formed integrally with the tubular body and wherein an inner surface of a proximal portion of said tubular body defines a reservoir for the medication,
a plunger slidably housed inside the tubular body and having a rod connected to a grasping means,
a piston slidably mounted to a portion of said rod and positioned in sealing contact with the inner surface of said tubular body, thereby providing a closure for the medication reservoir, wherein said piston has a longitudinal opening through which the rod of the plunger is disposed, and wherein said piston initially abuts on a stop means disposed within said tubular body in the form of a projection on the inner surface of the tubular body when the applicator is received by the user,
a coupling means for grasping and holding said piston on said rod,
a removable closure means for sealingly-closing off said opening on said dispensing end,
wherein the plunger is extractable from the tubular body until the rod becomes engaged with the piston by the coupling means, whereupon the plunger together with the piston is displaceable along the tubular body towards the dispensing end for expelling the medication through the opening.

2. The applicator according to claim 1, wherein an annular projection is provided as the stop means.

3. The applicator according to claim 1, wherein a distal portion of the tubular body increases slightly in diameter between the stop means and the grasping end to allow air to escape during assembly of the applicator.

4. The applicator according to claim 1, wherein said removable closure means comprises a cap.

5. The applicator according to claim 1, wherein the plunger, the rod and the grasping means are one piece.

6. The applicator according to claim 1, wherein the dispensing end of the tubular body is provided with a plurality of openings, covered by a removable cap.

7. The applicator according to claim 6, wherein cap is provided on its inner surface with a plurality of projections which fit into the openings on the dispensing end of the tubular body.

8. The applicator according to claim 1, wherein the stop means in the form of a projection on the inner surface is provided about midway of the tubular body, and wherein the length of the plunger corresponds essentially to the length of the tubular body.

9. The applicator according to claim 1, wherein said piston comprises an essentially cylindrical central body having a thru hole and a sealing flange which completely encircles said central body, leaving a channel between said central body and said sealing flange, and wherein said sealing flange has an annular lip on its outer surface.

10. The applicator according to claim 9, wherein the central body of said piston ends at an upper end thereof in a rounded projection which is similar in shape to the dispensing end of the applicator to minimize the amount of medication that is not dispensed.

11. The applicator according to claim 1, wherein said grasping means of said plunger comprises a ring.

12. The applicator according to claim 1, wherein the rod has a diameter sized to slidably move through the longitudinal opening of the piston and contains interaction elements with the piston, which rod is the prolongation of a cruciform shaped rod which is slightly smaller in width than an inner diameter of the tubular body, and wherein said cruciform shaped rod ends in a ring to facilitate operation of the plunger.

13. The applicator according to claim 1, wherein the grasping end of the tubular body extends radially outwardly forming an annular flange to aid the user in holding the applicator.

14. The applicator according to claim 4, wherein an open end of the cap flares outwardly, thereby forming a radially outwardly extending annular flange to aid the user in removing said cap.

15. The applicator according to claim 4, wherein said cap is additionally provided with one or more inner annular projections on an inner wall thereof to improve sealing action.

16. The applicator according to claim 12, wherein an annular recess is provided on a proximal end of the longitudinal opening for interaction with an annular rib on an end of the rod and an annular projection is provided on a distal end of the longitudinal opening for interaction with a groove on the rod.

17. A medication applicator comprising:
a tubular body having a proximal portion with a rounded dispensing portion having at least one medication dispensing opening, a distal portion having a plunger opening, and a piston retainer disposed within said tubular body;
an elongated plunger having a piston portion and a handle portion slidably housed in said tubular body, said piston portion having a piston retainer at a distal portion thereof;
a piston having a through hole slidably mounted on said piston portion and being sized to sealingly contact at least a portion of an inner wall of said tubular body, said piston being capable of releasably engaging said tubular body piston retainer when said plunger is located in selected positions and engaging said plunger piston retainer when said plunger is located in selected positions; and
a handle connected to said plunger to facilitate sliding movement thereof.

* * * * *